United States Patent
Ekstrom

(10) Patent No.: US 8,425,483 B2
(45) Date of Patent: Apr. 23, 2013

(54) DOUBLE GUSSET CLOTH DIAPER ALONG WITH METHOD FOR MAKING THE SAME

(75) Inventor: Julie Ekstrom, Littleton, CO (US)

(73) Assignee: Kanga Care, LLC, Littleton, CO (US)

( * ) Notice: Subject to any disclaimer, the term of this patent is extended or adjusted under 35 U.S.C. 154(b) by 563 days.

(21) Appl. No.: 12/391,889

(22) Filed: Feb. 24, 2009

(65) Prior Publication Data

US 2009/0216209 A1  Aug. 27, 2009

Related U.S. Application Data

(60) Provisional application No. 61/031,949, filed on Feb. 27, 2008.

(51) Int. Cl.
*A61F 13/15* (2006.01)

(52) U.S. Cl.
USPC ............ 604/385.14; 604/385.28; 604/385.15; 604/385.19; 604/385.25; 604/385.24

(58) Field of Classification Search ............ 604/385.14, 604/385.28, 385.15, 385.19, 385.25, 385.24
See application file for complete search history.

(56) References Cited

U.S. PATENT DOCUMENTS

| | | | |
|---|---|---|---|
| 3,667,466 A * | 6/1972 | Ralph ........................... | 604/364 |
| 3,710,797 A | 1/1973 | Marsan | |
| 4,695,278 A | 9/1987 | Lawson | |
| 4,795,454 A | 1/1989 | Dragoo | |
| 4,808,177 A | 2/1989 | DesMarais et al. | |
| 4,981,480 A | 1/1991 | Gaudet et al. | |
| 5,106,382 A | 4/1992 | Henry | |
| 5,295,986 A | 3/1994 | Zehner et al. | |
| 5,489,282 A | 2/1996 | Zehner et al. | |
| 5,613,959 A * | 3/1997 | Roessler et al. ............... | 604/364 |
| 5,827,259 A | 10/1998 | Laux et al. | |
| 5,904,675 A | 5/1999 | Laux et al. | |
| 5,993,433 A | 11/1999 | St. Louis et al. | |
| 6,254,583 B1 * | 7/2001 | Coates ..................... | 604/385.14 |
| 6,264,639 B1 | 7/2001 | Sauer | |
| 6,579,273 B2 | 6/2003 | Dupuy | |
| 2006/0206086 A1 * | 9/2006 | Lavon et al. ............. | 604/385.14 |
| 2008/0065039 A1 | 3/2008 | Labit et al. | |

OTHER PUBLICATIONS

Best Cloth Diapers Online—Rump-a-Rooz Diaper Review dated Dec. 13, 2007, obtained from http://www.clothdiapersites.com/index.php?a=stats&u=rumparooz&all_reviews=1 on Feb. 8, 2011, 8 pp.

Diaper Sewing Divas—How I Sew Internal Gussets dated Jan. 14, 2008, obtained from http://www.diaperdivas.proboards.com/index.cgi?board=sticky&action=display&thread=3659 on Feb. 28, 2011, 16 pp.

(Continued)

*Primary Examiner* — Jacqueline F. Stephens
(74) *Attorney, Agent, or Firm* — Holland & Hart LLP

(57) ABSTRACT

A double gusset cloth diaper including an inner surface and an outer surface forming an hourglass shape, having a groin area proximate a center line of the reusable diaper and defining at least one recess therebetween. A fluid absorbent material is removably located in the recess through the opening. A first gusset is attached to the reusable diaper to form a first seal between the inner surface and the legs of the user. A second gusset is attached to the reusable diaper proximate the first gusset. The gussets are formed of an elastic material attached to the wrong side of the inner surface in a channel formed by stitching the inner surface to form channels.

18 Claims, 5 Drawing Sheets

OTHER PUBLICATIONS

Blueberry, One Size Minky Pocket Diaper. Downloaded at http://www.blueberrydiapers.com on May 4, 2007.

Yahoo! Groups; Group Discussion and Diaper Pattern; http://groups.yahoo.com/group/sewyourowndiapers/message/79243; May 13, 2003; 5 pp.

Yahoo! Groups; Published Message Post; http://groups.yahoo.com/group/sewyourowndiapers/message/79243; Jan. 7, 2001; 3 pp.

Yahoo! Groups; Published Message Post; http://groups.yahoo.com/group/sewyourowndiapers/message/25872; Jul. 12, 2000; 2 pp.

* cited by examiner

DOUBLE GUSSET CLOTH DIAPER ALONG WITH METHOD FOR MAKING THE SAME

FIELD OF THE INVENTION

The technology of the present application relates generally to cloth or reusable diapers and, more particularly, to providing a double gusset on the cloth or reusable diaper to further inhibit fluid from leaking.

BACKGROUND

Many forms of protective garments are available today. Such protective garments include, for example, disposable diapers, reusable diapers, training paints, and the like. Each of these protective garments has an absorbent pad located proximate the groin of the person wearing the protective garment. Many absorbent pads are used in a single wearing and discarded after use. Some absorbent pads, such as those used with many reusable diapers, are washable to allow for reuse if desired.

While the absorbent pad is effective in absorbing a portion of any fluid, such as, for example, urine, it typically is incapable of immediately wicking the fluid from the surface of the diaper. Thus, diapers include a seal around, for example, leg openings to inhibit fluid from leaking past the leg openings to allow the urine to be wicked into the absorbent pad.

The most common complaint regarding cloth or reusable diapers relates to fluid leaking past the seal formed around the leg openings. Fluid leaking past the seal, typically formed of an elastic material coupled to the interior of the cloth diaper to hold the cloth snuggly to the leg of an infant or individual, can be messy and can be a health risk. This is especially true if the absorbent pad and/or cloth becomes saturated with fluid.

Thus, against this background, it would be desirable to provide a cloth or reusable diaper with an improved seal to inhibit leakage.

SUMMARY

Aspects of the technology of the present application include, for example, a reusable diaper. Generally, the double gusset cloth diaper includes an inner surface and an outer surface forming an hourglass shape, having a groin area proximate a center line of the reusable diaper and defining at least one recess therebetween. An opening in the inner surface provides access to the recess. A fluid absorbent material is removably located in the recess through the opening. The hourglass shape of the reusable diaper includes edge margins adapted to contact the legs of a user. A first gusset is attached to the reusable diaper about the edges adapted to form a first seal between the inner surface and the legs of the user. The first gusset is formed of an elastic material attached to the rough side of the inner surface in a channel formed by stitching the inner surface to form channels proximate the edges. A second gusset is attached to the reusable diaper proximate the first gusset. The second gusset is formed of an elastic material attached to the rough side of the inner surface in a channel formed by stitching the inner surface to form channels such that the second gusset is located between the first gusset and the groin area. The second gusset forms a second seal between the inner surface and the legs of the user to further inhibit fluid from leaking.

One embodiment of a double gusset diaper includes an exterior panel having a surrounding outer edge margin. An interior panel superposable with the exterior panel is joined to a majority of the outer edge margin. A first pair of elasticized gussets is disposed along the outer edge margin and adapted to engage a wearer's legs. A second pair of elasticized gussets, which are substantially parallel to each other, is disposed between the first pair of gussets. The interior panel may include a slit sized and adapted to receive an absorbent material therethrough such that it is interposed between the interior and exterior panels.

The diaper includes a front waistband portion, a rear waistband portion, and an intermediate portion extending between the front and rear waistband portions. The intermediate portion includes first and second arcuate side margins for confronting a wearer's legs. The first and second pairs of gussets each define a respective first and second auxiliary containment region therebetween, and each pair of gussets extends along an associated one of the first and second side margins.

The diaper includes a plurality of fasteners disposed on the front waistband portion and on the rear waistband portion operative to secure the diaper to a wearer. The fasteners may be cooperative snaps, hook and loop material, or adhesive tape, to name a few.

A protective garment system is contemplated that includes a diaper with an exterior panel comprising polyurethane laminate material and having a surrounding outer edge margin. An interior panel comprising micro-chamois material is joined to a majority of the outer edge margin.

A first pair of sealing means is disposed along the outer edge margin operative to engage the legs of a wearer and a second pair of sealing means is disposed between the first pair of sealing means. The system includes at least one absorbent pad removably insertable between the interior and exterior panels. The pad may be comprised of hemp material, for example. The system may include a pair of configurable absorbent pads that include cooperative fasteners for coupling the pads together.

Also contemplated is a method for making a diaper, including the step of attaching a first elastic strip to an interior panel, where the interior panel has a perimeter that includes first and second side margins for confronting a wearer's legs; the first elastic strip being offset inwardly from the side margins and attached to the interior panel at two or more locations. Also, a second elastic strip is attached at two or more locations along at least one of the side margins. An exterior panel is joined to the interior panel around a majority of the perimeter. The method may also include the step of attaching a third elastic strip to the interior panel at two or more locations and offset inwardly from the side margins.

Further aspects and features of the technology of the present application will become apparent from the detailed description provided below. In addition, any one or more aspects of the technology of the present application may be implemented individually or in combination with any one or more of the other aspects of the technology of the present application. It should be understood that the detailed description and examples provided therein are intended for purposes of illustration and should not be considered limiting.

BRIEF DESCRIPTION OF THE DRAWINGS

The drawings described herein are for illustration purposes and are not intended to limit the scope or spirit of the technology of the present invention.

DETAILED DESCRIPTION

The technology of the present application will now be described with reference to the figures. Although described in the context of a cloth diaper, one of ordinary skill in the art would recognize that the technology may be used for other reusable protective garments. Moreover, the technology of the present application is explained with reference to exemplary embodiments. The word "exemplary" is used herein to mean "serving as an example, instance, or illustration." Any embodiment described herein as "exemplary" is not necessarily to be construed as preferred or advantageous over other embodiments. Additionally, unless otherwise provided, all embodiments provided herein should be considered exemplary.

Figure 1:
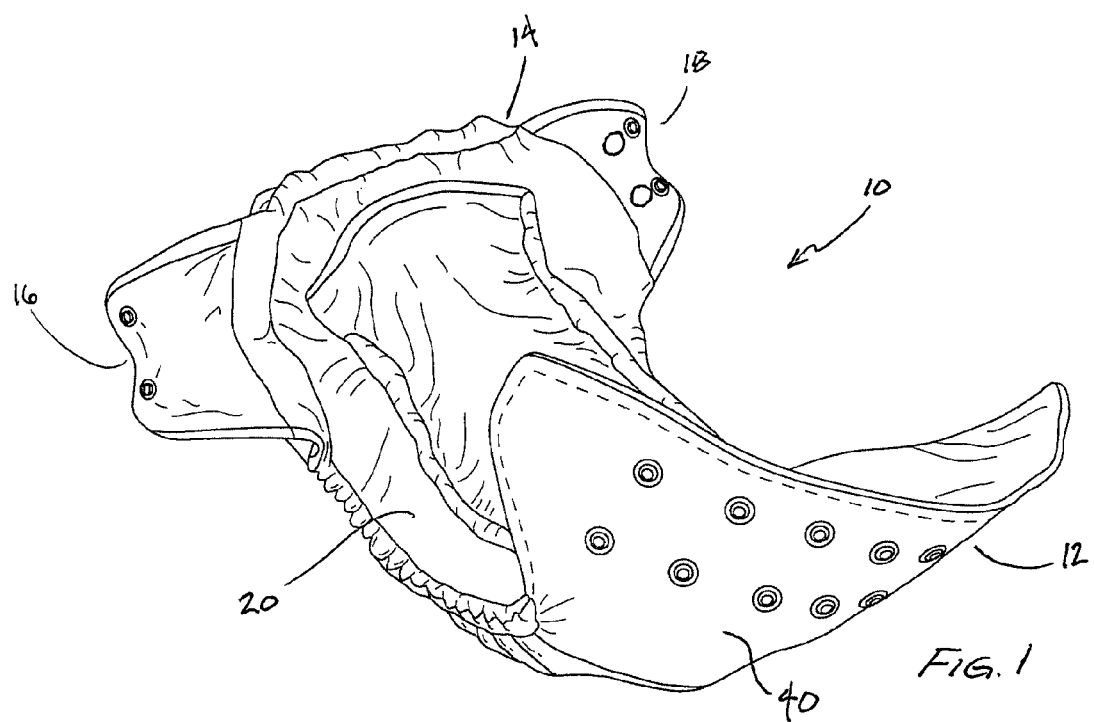
FIG. 1 is a perspective view of a double gusset cloth diaper according to an exemplary embodiment.

FIG. 1 illustrates an exemplary embodiment of a double gusset cloth diaper 10. Diaper 10 includes a front waistband portion 12 and a rear waistband portion 14. Diaper 10 also includes an exterior panel 40 having a surrounding outer edge margin and an interior panel 20 joined to a majority of the outer edge margin. Diaper 10 includes tabs 16 and 18 which support fasteners for securing the diaper to a wearer. Preferably, tabs 18 and 16 are constructed from an elastic or resilient material such as spandex.

Figure 2:
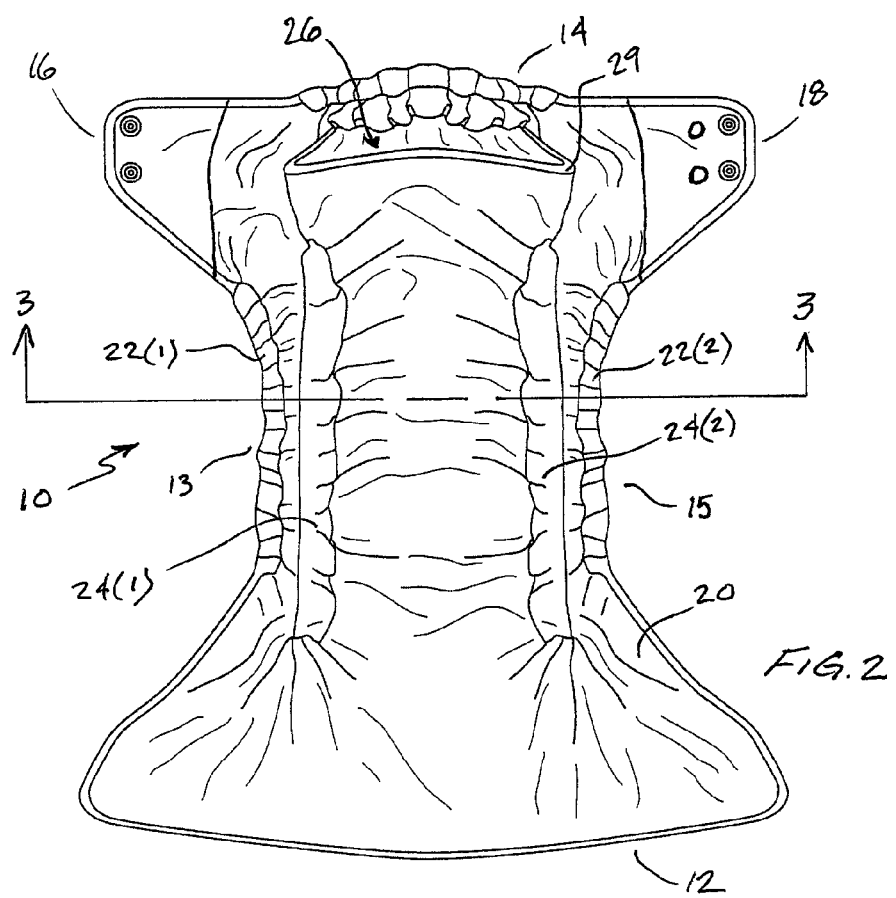
FIG. 2 is a top plan view of the double gusset diaper illustrating the interior of the diaper.

FIG. 2 is a view of diaper 10 looking down on the rough side of interior panel 20. Interior panel 20 is comprised of a micro-chamois material. One of ordinary skill in the art will recognize other materials are possible. The outer edge margin of diaper 10 includes side margins 13 and 15 which are configured to confront the legs of a wearer. In this case side margins 13 and 15 correspond to right and left legs respectively. The side margins 13 and 15 are generally arcuate as shown, but could have other shapes. A first pair of gussets 22(1) and 22(2) is disposed along the arcuate side margins 13 and 15 respectively. A second pair of gussets 24(1) and 24(2) is disposed between the first pair of gussets 22(1) and 22(2). It can be seen in FIG. 2 that the first pair of gussets extends along the arcuate edge margins 13 and 15, while the second pair of gussets are approximately parallel to each other and offset inward from the first pair of gussets. Second pair of gussets 24(1) and 24(2), alternatively, may conform to the shape or arc of first pair of gussets 22(1) and 22(2).

Figure 3:
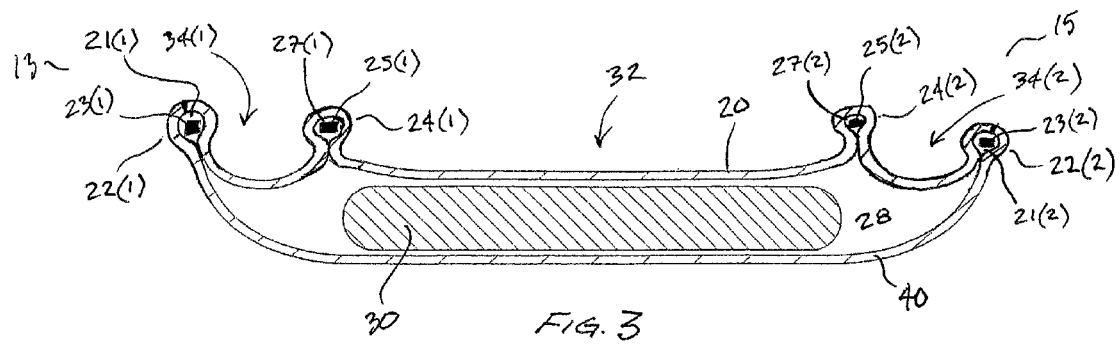
FIG. 3 is a cross-section of the double gusset diaper taken about line 3-3 as shown in FIG. 2.

With further reference to FIG. 3, it can be seen that interior panel 20 also includes an opening 26 for receiving an absorbent material, shown here in the form of a pad 30, such that it is interposed between interior panel 20 and exterior panel 40 in the interior 28 of diaper 10. Opening 26 may be in the form of a slit with an accompanying elastic member 29. The opening 26 may be reinforced by placement of reinforcing material, such as additional micro-chamois material, about the opening cut in the interior panel 20. Opening 26 optionally may have a closure flap (not shown) as is generally known in the art; although a closure flap inhibits access to interior 28 and may hinder removal of soiled pad 30. As shown in FIG. 3, it can be appreciated that the second pair of gussets 24(1) and 24(2) define a first or primary containment region 32. The first pair of gussets 22(1) and 22(2), in conjunction with the second pair of gussets, defines a pair of auxiliary (or secondary) containment regions 34(1) and 34(2). For example, with reference to the right arcuate side margin 13, gusset 22(1) and 24(1) create first auxiliary containment region 34(1). In this embodiment, each gusset 22(1), 22(2), 24(1), and 24(2) includes a channel 21(1), 21(2), 27(1), and 27(2) respectively. Disposed in each of these channels is a respective elongate elastic member 23(1), 23(2), 25(1), and 25(2).

Figure 4:
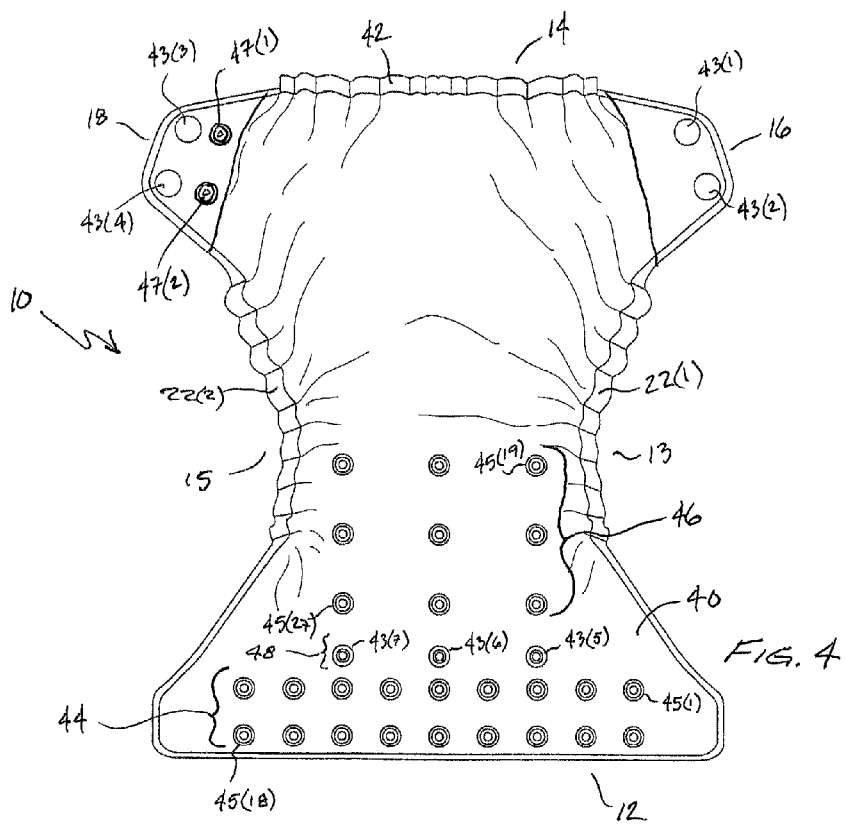
FIG. 4 is a bottom plan view of the double gusset diaper illustrating the exterior of the diaper.
Figure 5:
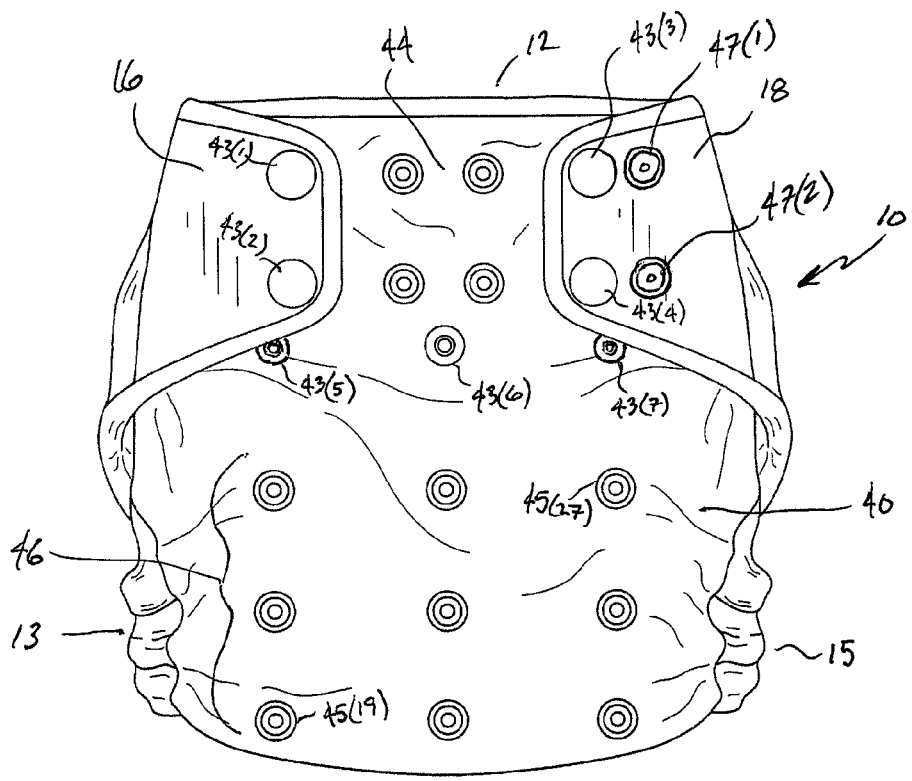
FIG. 5 is a front view in elevation of the double gusset diaper configured as it would be worn by a wearer.

With reference to FIG. 4, the double gusset diaper 10 includes a plurality of fasteners disposed on the exterior panel 40 for fastening the diaper to a wearer as well as for adjusting the waist size and rise of the diaper to better conform to different sized wearers. For example, a pattern of fasteners 44 is provided along the front waistband portion 12 of diaper 10, which is operative to fasten the diaper 10 to a wearer as well as to accommodate different waist sizes. In this case, the fasteners are cooperative snaps comprising female sockets and mating male studs. Pattern 44 includes sockets 45(1)-45(18). As can be better appreciated with further reference to FIG. 5, sockets 45(1)-45(18) are placed such that when the diaper is being worn, they are in a position to receive studs 43(1)-43(4). It can be appreciated that pattern 44 provides multiple locations at which tabs 16 and 18 may be fastened to front waistband portion 12. Each column of pattern 44 may receive a corresponding pair of studs 43. Accordingly, the waistband is adjustable in diameter such that it can conform to different waist sizes for larger and smaller wearers. While pattern 44 is shown here as an array of studs, the positions of the studs and mating sockets could be reversed. Also, shown in FIGS. 4 and 5 are additional sockets 47(1) and 47(2), which may receive studs 43(1) and 43(2) respectively when diaper 10 is worn by a person with a waist sized such that in order to fit properly about their waist, tab 16 must overlap tab 18.

The rise of diaper 10 is also adjustable by employing socket pattern 46. Pattern 46 in this case, includes sockets 45(19)-45(27). Each row of pattern 46 may engage stud pattern 48, which includes studs 43(5)-43(7). Accordingly, in this case, there are three rise adjustment rows. It should be understood that while the patterns are shown here with a particular number of rows and columns, the number of rows and/or columns may vary as well as the corresponding number of mating fasteners. Furthermore, different types of fasteners may be used other than those shown here. For example, cooperative hook and loop material, such as Aplix® 800, may be employed for the waistband adjustment and/or rise adjustments as is described more thoroughly below.

Figure 6:
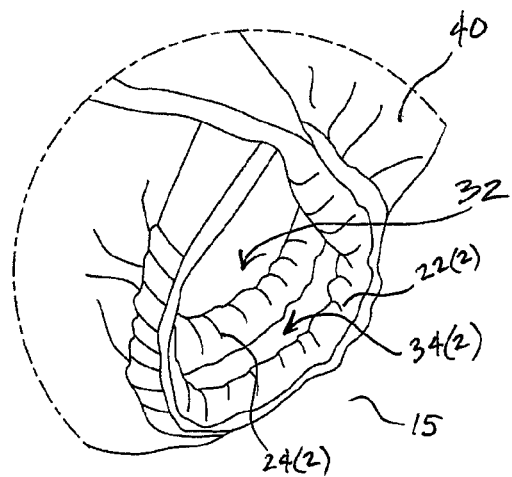
FIG. 6 is an enlarged partial perspective view of the left leg opening.

FIG. 6 is an enlarged view of left arcuate side margin 15 that, when in the worn state, substantially surrounds a left leg opening of diaper 10. As shown, gussets 22(2) and 24(2) provide a double gusset which confronts a wearer's leg. This double gusset arrangement provides for both the primary containment region 32 and the auxiliary containment region 34(2). Accordingly, the double gusset arrangement provided herein provides an added measure of containment in that if liquid and/or solid waste escapes from containment region 32 past gusset 24(2), gusset 22(2) will retain such spills in auxiliary containment region 34(2).

Figure 7:
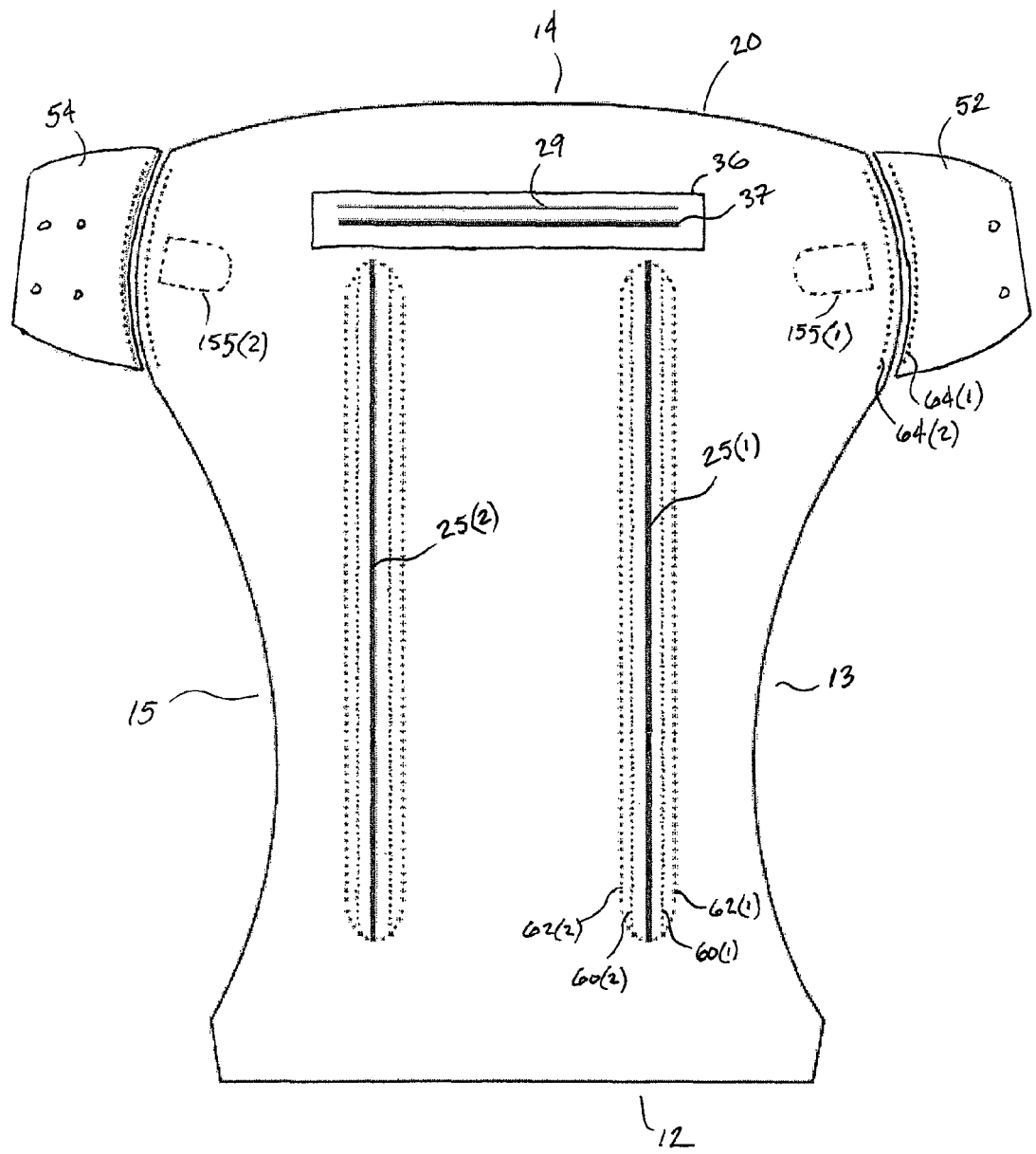
FIG. 7 is a top plan view of a pattern detail of an interior panel as viewed from the rough side.

With initial reference to FIG. 7, a method for making a reusable diaper with double gussets is provided. Interior panel 20 is made from a micro-chamois material having an overall length of approximately 19.5 inches and an overall width of 15.75 inches while the provided size is for typically babies or toddlers, the diaper may be sized accordingly for smaller babies, e.g., premature, older children, or even adults. Interior panel 20 may be prepared as shown in FIG. 7 by marking the cuts and then cutting out the shapes and openings. This may be facilitated by a pattern template similar to that shown in FIG. 7. Throughout the description of the methods, the side of each piece that faces the interior 28 of the diaper is referred to as the wrong or rough side. Conversely, the side of each piece that is opposite the interior 28 of diaper 10 is referred to as the right or finish side of the material.

Viewing interior panel 20 from the rough side, as shown in FIG. 7, the construction of the inner gussets 24(1) and 24(2) is described. Elongate elastic members 25(1) and 25(2) are sewn to the interior panel. Elastic members 25(1) and 25(2) comprise ⅛ inch elastic and have a length of approximately 5.5 inches when in the relaxed state although other sizes of elastic are usable. Starting at the end closest to waistband portion 14, the elastic members are tacked down using a forward and backward straight stitch to secure the elastic to the fabric. While the below descriptions are generally with relation to stitching, and in some cases specific stitches, one of ordinary skill in the art will recognize on reading the disclosure that other stitches may be used. Also, instead of stitching, connections may be made using adhesives, glues, tapes, welds, or the like. As an example, elastic piece 25(1) is attached to the inner surface by zigzagging the stitch along the length of the elastic. Ideally, the stitch is just wide enough to zigzag over the elastic and catch on each side. The elastic is stretched as it is stitched into place resulting in a finished length of approximately 13 inches. At the end of the elastic member, a straight stitch is used to tack down the end of the elastic with forward and backward stitches. Elastic member 25(2) is attached to interior panel 20 in substantially the same manner.

Next, each elastic member 25(1) and 25(2) is sewn into a channel 27(1) and 27(2) respectively. For instance, the wrong sides of the fabric are folded together using elastic member 25(1) as a fold line to form a channel in which the elastic resides. Once folded, stitch guides 60(1) and 60(2) will overlap each other. Similarly, stitch guides 62(1) and 62(2) will overlap. Starting at the end closest to the rear waistband portion 14, stitching is sewn along the full length of the elastic along stitch lines 60(1) and 60(2). A straight stitch is also sewn along stitch guides 62(1) and 62(2), which is ¼ inch out from the stitch guides 60(1) and 60(2). Channel 27(2) is formed around elastic member 25(2) in substantially the same way as described with respect to channel 27(1) above.

Stretch tabs 52 and 54 are attached to interior panel 20 by placing the finish side of interior panel 20 facing up (opposite that shown in FIG. 7) and the finish side of tab 52 down against the finish side of interior panel 20. The ends of the materials are serged together along seam lines 64(1) and 64(2), which are aligned with each other. The attachment procedure for tab 54 is substantially the same as that for tab 52.

With the finish side of interior panel 20 facing up (opposite that shown in FIG. 7), pocket opening reinforcement piece 36 is placed finish side down. Reinforcement piece 36 is approximately 1.5×8 inches of micro-chamois and includes a cut that lines up with cut 37. A straight stitch is sewn ⅛ inch from cut 37 around the full perimeter of the cut. The finish side of the interior panel 20 is placed down and the reinforcement piece 36 is pulled through cut 37. Reinforcement piece 36 is then top stitched to the rough side of interior panel 20. Reinforcement piece 36 is sewn around its perimeter at approximately ⅛ inches from the edge. Elastic member 29 is encased between the reinforcement piece and interior panel 20. Each end of elastic member 29 is tacked down as the reinforcement piece is top stitched. Elastic piece 29 is ⅛ inch elastic and is approximately 3.5 inches long in the relaxed state. Once fully stretched, elastic piece 29 should be approximately 7 inches long corresponding to the length of cut 37.

Figure 8:
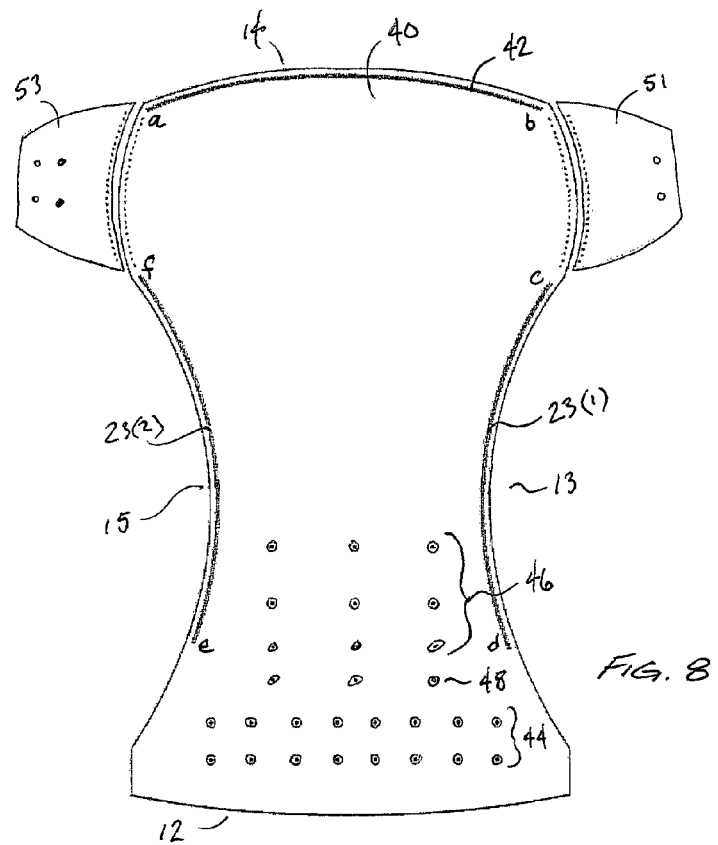
FIG. 8 is a top plan view of a pattern detail of an exterior panel as viewed from the finish side.

Referring now to FIG. 8, preparation and attachment of the exterior panel 40 is discussed. Exterior panel 40 is comprised of polyurethane laminate material (PUL). The exterior panel is shown in FIG. 8 with the finish side up. Initially, both the stud and socket snap fasteners of patterns 44, 46, and 48 are attached to the finish side of the exterior panel 40. Stretch tabs 51 and 53 are attached to exterior panel 40 in substantially the same way as tabs 52 and 54 were attached to interior panel 20, as described above.

Exterior panel 40 is placed with the finish side of the fabric up as shown in FIG. 8 and interior panel 20 is placed directly on top with the rough side of the fabric up as shown in FIG. 7. At this point, the finish sides of both panels are touching. The full perimeter of the diaper is serged together. As the perimeter of the diaper is serged together, the tip of elastic piece 42 is attached at point "a." The remaining free end of elastic piece 42 is attached at point "b." At point "c", the tip of elastic piece 23(1) is attached. The remaining free end of elastic piece 23(1) is attached at point "d." The tip of elastic piece 23(2) is attached at point "e" and the remaining free end of elastic piece 23(2) is attached at point "f", just before the diaper body meets the bottom of stretch tab 16. Elastic pieces 42, 23(1), and 23(2) are each made from ¼ inch elastic that is 5.5 inches long when in the relaxed state.

After the diaper is serged together, the diaper will be inside out. The diaper is turned right side out by pulling it through the pocket hole opening 26. The perimeter of the diaper is then top stitched clockwise along the rear waistband portion 14, stitching in ½ inch from the edge of the diaper. The elastic member 42 should be between the needle and the edge of the diaper. This creates a "channel" for the elastic to run in and gather the fabric around it. Except for portions of the perimeter that contain elastic, the perimeter is top stitched approximately ⅛ inches in from the edge of the diaper. Where elastic is encased, the perimeter is sewn approximately ½ inches in from edge of the diaper, thus, creating a "channel" for each elastic member.

With the inside or interior panel of the diaper facing up (the micro-chamois), 2 studs 43(1)-43(4) are attached to both the right 16 and the left 18 stretch tabs with the studs facing up and their caps facing down. With the inside of the diaper facing down (the micro-chamois), and using the guide line provided in the pattern template for placement, 2 sockets 47(1) and 47(2) are attached to the left stretch tab 18 with the sockets facing up and the caps facing down.

Figure 9:
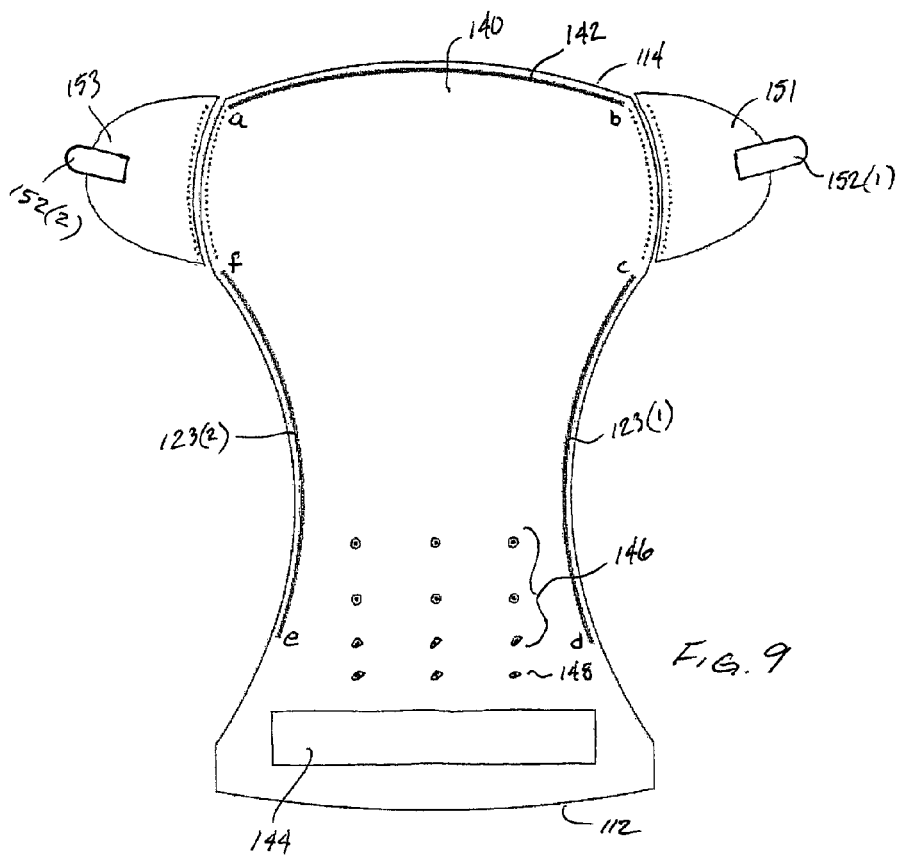
FIG. 9 is a top plan view of a pattern detail as viewed from the finish side illustrating an alternate construction of an exterior panel.

In an alternate construction, the waistband fasteners of pattern 44 are replaced with hook and loop style fasteners. In this case, the diaper is constructed similarly to that as described above. However, exterior panel 140 shown in FIG. 9, includes a strip of loop material in place of pattern 44. Also, tabs 16 and 18 are formed of spandex tabs 151 and 153, which have a rounded configuration. Tabs 16 and 18 each include one hook and one loop piece. Each hook and loop piece is die cut to 1×1.5 inches. With exterior panel 140 facing up, the loop pieces are facing up and the hook pieces are facing down. Accordingly, each stretch tab is sandwiched between hook and loop die cut pieces. In this construction, the finish side of the interior panel includes a pair of laundry tabs 155(1) and 155(2). Laundry tabs 155(1) and 155(2) are die cut loop pieces attached to the finish side of the interior panel as shown in FIG. 7. The laundry tabs provide a means to secure the hook material on the stretch tabs thereby preventing the hook material from snagging the soft micro-chamois material of the interior panel during washing.

Accordingly, the double gusset cloth diaper has been described with some degree of particularity directed to the exemplary embodiment. It should be appreciated, though, that the double gusset cloth diaper is defined by the following claims construed in light of the prior art so that modifications or changes may be made to the exemplary embodiment without departing from the inventive concepts contained herein.

What is claimed is:

1. A protective garment system, comprising:
   a. a reusable diaper including:
      i. an exterior panel comprising polyurethane laminate material and having a surrounding outer edge margin;
      ii. an interior panel comprising micro-chamois material and joined to a majority of said outer edge margin;
      iii. a first pair of sealing means disposed along said outer edge margin operative to engage the legs of a wearer, wherein said first pair of sealing means includes elongate elastic members sewn to said exterior panel;
      iv. a second pair of sealing means disposed between said first pair of sealing means, wherein said second pair of sealing means includes elongate elastic members sewn at least to said interior panel; and
   b. at least one absorbent pad removably insertable between said interior and exterior panels.

2. A protective garment system according to claim 1 wherein said pad is comprised of hemp material.

3. A protective garment system according to claim 1 including a pair of configurable absorbent pads.

4. A protective garment system according to claim 3 wherein said pads include cooperative fasteners for coupling said pads together.

5. A reusable diaper, comprising:
   a. an exterior panel having a surrounding outer edge margin, the exterior panel comprising a waterproof material;
   b. an interior panel superposable with said exterior panel and joined to a majority of said outer edge margin, the interior panel comprising a fluid-permeable material;
   c. a first pair of gussets coupled at least to the exterior panel and disposed along said outer edge margin and adapted to engage a wearer's legs, wherein the first pair of gussets include a first pair of elongate elastic members;
   d. a second pair of gussets disposed between said first pair of gussets, wherein each of said second pair of gussets includes an elastic member disposed in and coupled to a channel formed in said interior panel; and
   e. an absorbent pad adapted to be interposed between said exterior panel and said interior panel.

6. A reusable diaper of claim 5 wherein a first containment region is formed by the second pair of gussets.

7. A reusable diaper of claim 6 wherein a pair of second containment regions are formed between the first pair of gussets and the second pair of gussets.

8. A reusable cloth diaper, comprising:
   a. an exterior panel comprising a waterproof material and having a surrounding outer edge margin;
   b. an interior panel comprising a fluid permeable material that is substantially a same size and shape as the exterior panel and joined to a majority of the exterior panel at the outer edge margin;
   c. a first pair of sealing means disposed along the outer edge margin operative to engage the legs of a wearer, wherein the first pair of sealing means includes elongate elastic members coupled to said exterior panel;
   d. a second pair of sealing means disposed between the first pair of sealing means, wherein the second pair of sealing means includes elongate elastic members coupled at least to the interior panel; and
   e. at least one absorbent pad removably insertable between the interior and exterior panels.

9. A reusable diaper according to claim 8 wherein the second pair of gussets are substantially parallel to each other.

10. A reusable diaper according to claim 8 wherein the interior panel includes a slit sized and adapted to receive the absorbent material therethrough.

11. A reusable diaper according to claim 8 wherein the second pair of sealing means further comprises a channel formed in the interior panel and the second pair of sealing means is disposed in the channel.

12. A reusable diaper according to claim 8 including a plurality of fasteners disposed on a front waistband portion and on a rear waistband portion operative to secure the diaper to a wearer.

13. A reusable diaper according to claim 12 wherein the fasteners are selected from the group consisting of cooperative snaps, hook and loop material, and adhesive tape.

14. A method for making a reusable diaper, the method comprising the steps of:
   providing a waterproof exterior panel that has a first perimeter defined by a size and a shape including first and second side margins, and a fluid-permeable interior panel that has a second perimeter including third and fourth side margins and is substantially a same size and shape as the waterproof exterior panel where the first and second side margins are superposable with the third and fourth side margins;
   attaching a first pair of elongate elastic strips to the fluid-permeable interior panel, the first pair of first elastic strips being offset inwardly from the third and fourth side margins and attached to the interior panel at two or more locations;
   forming a pair of channels in the fluid-permeable interior panel by folding the fluid-permeable interior panel about the first pair of first elongate elastic strips attached to the fluid permeable interior panel;
   attaching a second pair of elastic strips at two or more locations on the waterproof exterior panel, the second pair of elastic strips being attached along at least one of the first and second side margins; and
   joining the waterproof exterior panel to the fluid-permeable interior panel around a majority of the perimeter.

15. A method of claim 14 further comprising forming an opening to allow access to a space between the waterproof exterior panel and the fluid-permeable interior panel.

16. A method of claim 15 further comprising inserting an absorbent material in the space.

17. A method of claim 14 wherein the first pair of elongate elastic strips are sewn to the fluid-permeable interior panel.

18. A method of claim 17 wherein the second pair of elongate elastic strips are sewn to the waterproof exterior panel.

* * * * *

UNITED STATES PATENT AND TRADEMARK OFFICE
CERTIFICATE OF CORRECTION

Page 1 of 1

| | |
|---|---|
| PATENT NO. | : 8,425,483 B2 |
| APPLICATION NO. | : 12/391889 |
| DATED | : April 23, 2013 |
| INVENTOR(S) | : Ekstrom |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 686 days.

Signed and Sealed this
Ninth Day of December, 2014

Michelle K. Lee
*Deputy Director of the United States Patent and Trademark Office*